US010837814B1

United States Patent
Huang et al.

(10) Patent No.: US 10,837,814 B1
(45) Date of Patent: Nov. 17, 2020

(54) SMART GAS CYLINDER CAP

(71) Applicants: Liji Huang, Santa Clara, CA (US); Alok Batra, San Jose, CA (US); Venkata Sai Tejeswar Pokkuluri, San Jose, CA (US); Chih-Chang Chen, Cupertino, CA (US)

(72) Inventors: Liji Huang, Santa Clara, CA (US); Alok Batra, San Jose, CA (US); Venkata Sai Tejeswar Pokkuluri, San Jose, CA (US); Chih-Chang Chen, Cupertino, CA (US)

(73) Assignee: Siargo Ltd., Santa Clara, CA (US)

( * ) Notice: Subject to any disclaimer, the term of this patent is extended or adjusted under 35 U.S.C. 154(b) by 0 days.

(21) Appl. No.: 16/572,951

(22) Filed: Sep. 17, 2019

(51) Int. Cl.
*G01F 1/68* (2006.01)
*G01F 1/696* (2006.01)
*G01N 33/00* (2006.01)
*G01F 1/684* (2006.01)
*F17C 13/06* (2006.01)
*F17C 13/02* (2006.01)

(52) U.S. Cl.
CPC .............. *G01F 1/696* (2013.01); *F17C 13/02* (2013.01); *F17C 13/06* (2013.01); *G01F 1/6845* (2013.01); *G01N 33/0004* (2013.01); *F17C 2205/0329* (2013.01); *F17C 2250/0443* (2013.01); *F17C 2250/0447* (2013.01); *F17C 2250/0486* (2013.01)

(58) Field of Classification Search
None
See application file for complete search history.

(56) References Cited

U.S. PATENT DOCUMENTS 8,342,018 B2 * 1/2013 Huang .................. G01F 1/6845
73/204.26

* cited by examiner

Primary Examiner — Harshad R Patel

(57) ABSTRACT

The design and structure of a smart gas cylinder valve cap coupled with a smart MEMS mass flow meter, an embedded iBeacon or RFID reader and a remote data transmission module, which is capable of formulating an Internet of Things (IoT) system, is demonstrated in the disclosure. The smart gas cylinder cap(s) can be directly used to replace the mechanical valve handwheel or directly attached to the top of the existing mechanical handwheel as a smart data relay, and the cap(s) can either be applied to a single or plural numbers of gas cylinders while the smart gas flow meter shall communicate with the smart gas cap as well as to relay gas consumption data to a designated data center or a "cloud" which can further interface with the users and suppliers of the gas cylinders. The system is beneficial for many of the existing gas cylinder applications such as construction gas process, medical gas racks, gas cylinders for food and beverage, and gas racks for electronics fabrication, where the gas cylinder status, gas consumption as well as cylinder logistics are critical for the applications.

14 Claims, 9 Drawing Sheets

SMART GAS CYLINDER CAP

BACKGROUND OF THE INVENTION

1. Field of the Invention

This invention generally relates to gas cylinder management, and it particularly relates to a mechanical valve coupled with a flow measurement apparatus that utilizes both wireless technology and micro-electro mechanical system (MEMS) mass flow sensing technology to manage the gas cylinders in medical, industrial process, and laboratory applications. This invention is further related to internet of things (IoT) that connect multiple devices and relay such information to a cloud computing in case of data and infrastructure management.

2. Description of the Related Art

There are large numbers of gas cylinders for variety of applications in medical usage, industrial process, food and beverage, fuel supply, and laboratory experiments. The gas cylinders are a pure mechanical apparatus, and its usage and status are relied on estimation or the information from two local mechanical pressure gauges that have very low accuracy due to their measurement principle. For most of the applications, the gas cylinders are often placed far away from where the gas is actually consumed. The user hence is not able to have easy access to the status of the gas cylinder, which may lead to a sudden cutoff on usage resulting in loss of efficiency of workmanship and even leading to some unexpected damages. For some laboratory applications with hazardous and expensive gases, the failure to properly close a gas cylinder valve may lead to leakage or loss of the gas that could generate undesirable consequences both economically and environmentally. In addition, for large manufacturing plant or in hospital, for example, the gas cylinders supplied by gas manufacturers are often shipped in a gas rack for the efficiency of usage. Each rack will have multiple gas cylinders that are pre-connected in serial. At the time of usage, one or more of the cylinders shall be opened manually by the operator, and after gas is consumed from the cylinder(s) in use, the user at the (remote) site could only judge by the process parameters and would have to suspend the usage and send an operator to the cylinder rack to manage the valve configuration via manually closing the consumed one first and then to open a new one or a plural number of new cylinders. The sequence of the action is critical since the consumed cylinder will have low pressure and if it is not closed first or properly, the pressurized gas from the new cylinder(s) will backfill the empty cylinder(s) instead of being directed to the desired pipeline. For the current cylinder rack configuration, the mechanical valves on each of the cylinders have no indication as for its open or close status, and in the practical case, the operator might not be the same personnel for each of the action. It is then a very inefficient process as the operator would spend quite some time to determine which cylinder is to close first before processing the next cylinder for supply.

A few attempts have been disclosed for management of a gas cylinder. For example, Masin (Masin J. V., Gas cylinder and RFID transponder assemblies and related methods having fixed transponder orientation, U.S. Pat. No. 8,618,938, Dec. 31, 2013) has taught a device that is embedded with a specially orientated RFID device to track the cylinder locations. Such a device can effectively manage the cylinder location within a manufacturer site but the actual cylinder usage status remained unknown. Fowler et al. (Fowler, Z., Gamard, S., Gunnay, M., and Oetinger, P., Method and apparatus for controlling gas flow from cylinders, U.S. Pat. No. 9,273,799, Mar. 1, 2016) showed an electronic manometer with a protection cap. The electronic manometer is employed to estimate and calculate the gas remaining in the cylinder which could then provide a timely alarm for the end of gas supply from the specific cylinder. While this approach does have a solution to monitor the consumption of gas in the cylinder, it however could only provide a local alarm which in many cases could not be accessed by the user. Although alternatively such data could easily be transmitted via a wireless tool to the end user(s), the estimation via a manometer would not be accurate enough and may provide some false alarms. And indeed, Wise (Wise, E. C., Method and apparatus for monitoring, communicating and analyzing the amount of fluid in a tank, U.S. Pat. No. 9,435,675, Sep. 6, 2016) has disclosed a device to monitor the remaining mass of a gas container. Inside the special device a flow meter is used to measure a plurality of flowrates that vary while being dispensed, and the embedded processor shall be used to determine the remaining mass and an indication shall then be generated by the device. However, the disclosed device for the gas consumption is based on a rolling mean or average of a plurality of non-continuous measured flow rate that may be quite deviated from the actual mass as it also requires the knowledge of the gas density, pressure and temperature. The disclosed device has a capability to be remotely connected to a system comprised of a robot and a software application for the remote gas data management. While this does provide values to the management of the logistics of the gas cylinders, it is only applicable for one single cylinder and the user(s) of the gas must be at the proximity to the gas cylinder in order to have the needed information. In addition, this device requires the presence of power source which is often short of supply in the practical applications.

In one conceptual disclosure (Peters., M. and Popp, G., Valve with handle including sensors and memory, WO 02/040914 A3, May 23, 2002), an unspecific sensor and an electronic memory is proposed to attach to the valve of a gas cylinder such that the sensor can monitor the open or close of the valve status, and then a timer is used to timing the span of the open status. The usage time can be subsequently stored into the electronic memory for future billing of usage or inventory control. This disclosure is again a local solution and applicable for the usage of a single gas cylinder. It also could not provide the gas consumption information as it is only a digital timer data logger. The user needs to be at the proximity of the cylinder in order to access or download the information. In case of the gas cylinder rack applications, these approaches shall be very expensive and unable to solve the issues for gas cylinder remote metering as well as to attain precise status information of each gas cylinder in the grouped cylinder rack delivery.

SUMMARY OF THE INVENTION

It is therefore the objective of the present disclosure to provide the design of an apparatus and the corresponding system. The invented apparatus and system shall be used to seamlessly replace the current mechanical manometers as well as the cylinder mechanical valve operation with desired functions. The invented apparatus shall also allow the gas cylinder user(s) to have remote digital access to the gas cylinder status as well as the precise gas consumption for a specific cylinder, or for a plural of gas cylinders connected in serial and delivered in the form of cylinder racks. The desired system shall remotely alert the user of each cylinder valve status, and the gas consumption data shall be measured directly and accurately without indirect estimation or excessive calculations. Furthermore, the apparatus shall be cost effective and/or comparable to that for the current existing mechanical manometers. The desired apparatus and the system shall also not add excessive parts but preferably a direct replacement of the current mechanical apparatus. The apparatus shall be preferably stand-alone with battery power, and provide the ability to wirelessly transmit desired information to remote users either at a designated location or a mobile site. It is further desirable that the cylinder valve status and gas consumption information can be relayed to the gas cylinder suppliers via the internet of things (IoT) scheme such that the gas cylinder inventory and supply chain can be efficiently managed, and the user's gas consumption will not be cutoff because of lacking the cylinder status knowledge in advance.

In one preferred embodiment, the disclosed apparatus shall have the cylinder valve be operated smartly and transmit its status digitally to the user via the IoT configuration and the MEMS mass flow meter for metrology of the gas consumption. The valve with the said smart operation is achieved by addition a smart cap or by replacement of the mechanical handwheel. The smart cap shall also include mechanical open/close status indicators and the capability of wirelessly transmitting the status to a local concentrator or directly to the user's preferred control data center. The mechanical signs of cylinder status shall be shown through a side-view window on the said smart cap. The operation of the valve shall be achieved by rotating the handwheel on the smart cap that shall enable the changes in a color bar code, and the color bar code shall be exhibited via the side-view window. In the preferably embodiment, the red color bar code shall represent open status and black color bar code shall represent close status. The mechanical indication of the cylinder status shall assist the operator to easily identify the cylinder status as in many prior cases such status is not obvious to the operator. The status indicator shall be particularly helpful for the cylinder rack operation where a plural number of gas cylinders are connected in serial, and the operation procedure critically requests all the empty cylinders should be at closed status before a new cylinder is opened.

In another preferred embodiment, the disclosed smart cap shall have the capability to wirelessly transmit the digital status to a local concentrator or directly to a user's preferred receiver. The said smart cap shall be installed to replace the existing handwheel of mechanical valve that controls the open or close of the pathway to the gas delivery of the cylinder. The preferred wireless transmission shall be via a low energy Bluetooth protocol. The embedded Bluetooth LE module inside the said smart cap shall be connected to a microcontroller unit (MCU) and a micro-switch. When the handwheel of the cap is rotated to open the valve, the micro-switch shall be triggered and the MCU shall be waken up to further initialize the Bluetooth and transmit the valve status. The valve status can be programmed with its unique identification serial number and the three distinct digital codes used for indicating open, in-use and close status, or two distinct digital codes used for indicating open and close status. The transmitted data from the Bluetooth shall be relayed to the local concentrator that shall further send the data to the cloud which can be readily accessed by the remote user in an active or inactive mode. In a preferred configuration, the Bluetooth module shall be operated in the iBeacon mode that is the lowest power mode such that a conventional coin battery could enable the operation for over one year of time period. When the embedded Bluetooth module operates at the iBeacon mode, the iBeacon shall be programmed to continuously transmit the data at a customized interval to the local concentrator.

In another preferred embodiment, the said smart cap can adapt the radio frequency identification (RFID) as the digital status data relayed to the concentrator or the preferred user data center. The RFID incorporated with the said smart cap shall not require portable power and therefore it would have a much longer service time as an added value to the best interests of the user. The said smart cap shall have dual RFID, one encoded with the open status and another with the close status. The RFID reader shall be incorporated with the said smart MEMS mass flow meter. For the best performance of portable power, the RFID shall be normally in sleep mode. When the said smart valve changed from one status to another, the said smart flow meter shall register the change and wake up to initialize the RFID reader and scan the status of the valve(s) to further register the valve status. And then the data is relayed to the local concentration for data transmission to the designated cloud.

In yet another preferred embodiment, the disclosed apparatus with the said smart cap coupled with the said smart MEMS mass flow meter shall be used to replace the current mechanical manometers for the gas cylinders. Whereas an intelligent route shall be formed and the efficiency of the workmanship with gas cylinders shall be substantially increased in a completely new horizon. The said smart MEMS mass flow meter shall integrate the concentrator as a subsystem. With this preferred configuration, the concentrator shall have a plural of options for the desired data transmission to the designated cloud. Such options shall be readily available for the users to select by depending on specific applications and/or local working environments. The desirable transmission function shall be in the form of an exchangeable module integrated with the said MEMS mass flow meter, and the module can be either LoRa, NB-IoT, WIFI, Bluetooth LE, GSM or Sigfox. The module could also further be exchangeable with a wired data interface module such as RS485 or 10-Link if a wired option is a must. The smart MEMS mass flow meter shall preferably have local data storage via a plural number of solid state memories with a local data port such that the gas consumption data can also be downloaded to a local smart device in case the wireless data or even the wired data transmission are at fault or failed. In addition to the remote programming function, the local port or wireless interface shall also allow the password to enable local smart device access or the access by a password protected APP such that the user can also program the said MEMS mass flow meter with the desired performance parameters for the gas cylinders. In an additional preferred arrangement, the local smart device shall be able to relay the data to the designated cloud or receive the instructions from the designated cloud, which shall host the database for desired gas cylinders.

In yet another preferred embodiment, the disclosed system shall have the smart cap to replace the handwheel of mechanical valve on each gas cylinder, where there is a single or a plural number of gas cylinders connected in serial in the form of a gas rack configuration. When the valve is opened, the mechanical status indicator on the said smart cap shall be changed from close to open status, and the cap shall simultaneously trigger the micro-switch that further trigger the change of the Bluetooth iBeacon broadcasting data from close to open. The MEMS mass flow meter shall start to measure the consumption of the gas from a specific cylinder while the meter shall send a wakeup call to the integrated concentrator which will then take the status of the valve, the gas flow rate and current totalized gas consumption data from the smart cap's iBeacon data. After these desired data are collected by the concentrator, it shall relay the data to the designated cloud, and then the concentrator shall go to the sleep mode to preserve the energy. The broadcasting data from smart cap shall change from the open status into the in-use status at a pre-set time period that can be programmed and pre-determined by the user. When the gas consumption measured by the smart MEMS mass flow meter is reaching the alarm level that can be pre-programmed by the user or be altered via the cloud, then the smart MEMS mass flow meter will again send a wakeup call to the concentrator and the local concentrator shall then start to collect the gas consumption data, current instant flowrate as well as the broadcasting data from the iBeacon of the said smart cap. These desired data shall be immediately transmitted to the cloud where the alarm will be sent to the designated user(s) and/or to the supplier(s). The user shall then dispatch the operator to the site to close the valve of the cylinder that has alarm triggered and open a new gas cylinder. Each of the said valves and the smart MEMS mass flow meter shall go through a new cycle of status broadcasting and data acquisition as described above.

In another preferred embodiment, the disclosed apparatus shall have a MEMS mass flow meter for metrology that can be directly attached to the gas cylinder after the pressure regulator. The MEMS mass flow meter shall measure the precise gas consumption in a single gas cylinder or a plural of gas cylinders, and relay the information to the remote user via a wireless transmission approach. The MEMS mass flow meter shall be a direct replacement for the mechanical manometer in the mechanical apparatus of gas regulator for gas cylinders while the mechanical pressure regulating valve and high-pressure mechanical gauge sensor for monitoring the pressure inside the cylinders shall be kept unchanged. The MEMS mass flow meter shall measure the totalized consumed gas directly and continuously without the necessity of additional temperature and pressure measurement or to average the flowrates being registered. The MEMS mass flow meter shall be preferably coupled with a or a plural number of smart caps which shall directly engage or replace the handwheel of the current mechanical valve that opens and closes the pathway for the gas delivery from the cylinder. The smart cap shall have both the mechanical indication of the open or close status for the cylinder and the capability of wirelessly transmitting the status information to a local concentrator which could be integrated with the MEMS mass flow meter.

In another preferred embodiment, the said MEMS mass flow meter shall be powered by battery as a stand-alone unit with the M EMS mass flow sensor for direct measurement of the gas consumption, instead of using the mechanical manometer to gauge the pressure inside the cylinder and estimate the consumption, the MEMS mass flow meter shall measure both the instant flowrate and the totalized flow mass such that the status of the gas consumption shall be more precisely registered since the MEMS mass flow meter is far sensitive as compared to the readings with the current mechanical manometer. The M EMS mass flow meter shall further have a solid state memory module that shall register the total gas consumption in each session that can be pre-set by the user and an alarm shall be sent to the user if the pre-set value is reached. The total consumed gas shall be further added up by the values at each session and such information can be timely relayed to the user and/or to the supplier. It shall also be retrieved upon user's enquiries. The MEMS mass flow meter further has the integrated gas recognition sensor that shall be operated by thermal conductivity metrology principle. The gas identity can be further relayed to the user in case the gas type in use would not be the desired one. Additionally, the body of the M EMS mass flow meter shall be made completely with metals and having the desired threads identical to that of the current gauge for the corresponding pressure regulators. The metal body of the MEMS mass flow meter can also be made alternatively in various forms with single or plurality of the inlet/outlet gas delivery ports that shall be compatible with the varieties of the pressure regulator models.

The present disclosure provides a new design of a gas cylinder automation management apparatus where the mechanical manometer is replaced by a smart MEMS mass flow meter coupled with the smart cylinder caps for engaging or replacing the handwheel of the mechanical valve. This disclosed apparatus shall be capable of continuously, efficiently and precisely metering the gas consumption in a single or a plural of gas cylinders with automatic data management via a cloud computing. It shall significant increase the efficiency of the workmanship with gas cylinders. These objectives and others mentioned of the present disclosure shall become readily apparent upon further review of the following drawings and specifications. And additionally, for those with the knowledge of the art, the disclosed gas apparatus could be further utilized for gas delivery metering or dispensing via a fixed gas sources or a gas generator.

BRIEF DESCRIPTIONS OF THE DRAWINGS

FIG. 1 is the priori art.

FIG. 2A is the explosive view of the smart cap disclosed for the engagement or replacement of the handwheel of mechanical valve for gas cylinders. The smart cap is embedded with a Bluetooth iBeakon and a logic chip that can digitally transmit the open or close status of the valve to a local concentrator and further relay the information to a data center or a cloud. Mechanical indicators are also built in for easy onsite inspection.

DETAILED DESCRIPTION OF THE PREFERRED EMBODIMENTS

For various industrial applications where gas is required for the process, such as construction, special electronic device process, hospital, and special laboratory, and when onsite gas generator is not available, the gas cylinders become the sole source for the gas supply. For a gas cylinder, a mechanical valve is a must device to control the gas delivery. These valves however require a close proximity to access their status. Especially for the gas cylinders delivered in group with plural numbers of cylinders are normally connected in serial, then the checking procedure for the status of each cylinder would be labor intensive. The mistakes of opening a new gas cylinder before closing an empty cylinder will cause gas backfill from the new cylinder to the empty cylinder, which can happen from time to time. For the safety purpose, the gas cylinders are often distant from its applicable site, therefore the required efforts for approaching the status information onsite is also time consuming. The inquired valve status is also associated to the desired information of the gas consumption for the interested gas cylinders. These issues will not be possible to be solved for the existing mechanical devices. Therefore, the present disclosure shall address these and all the additional management demands for the gas cylinder applications.

Figure 1:
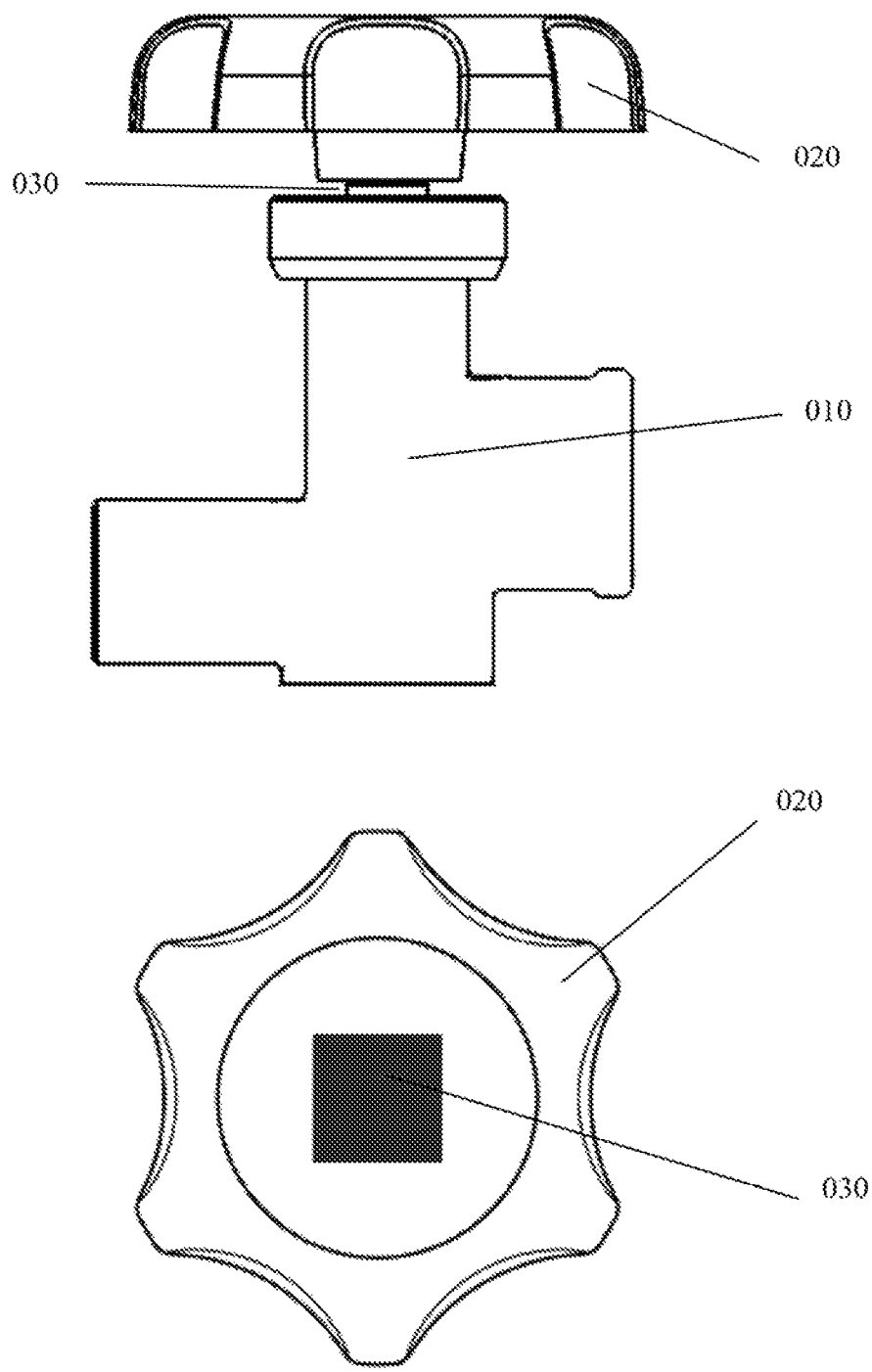
Figure 2A:
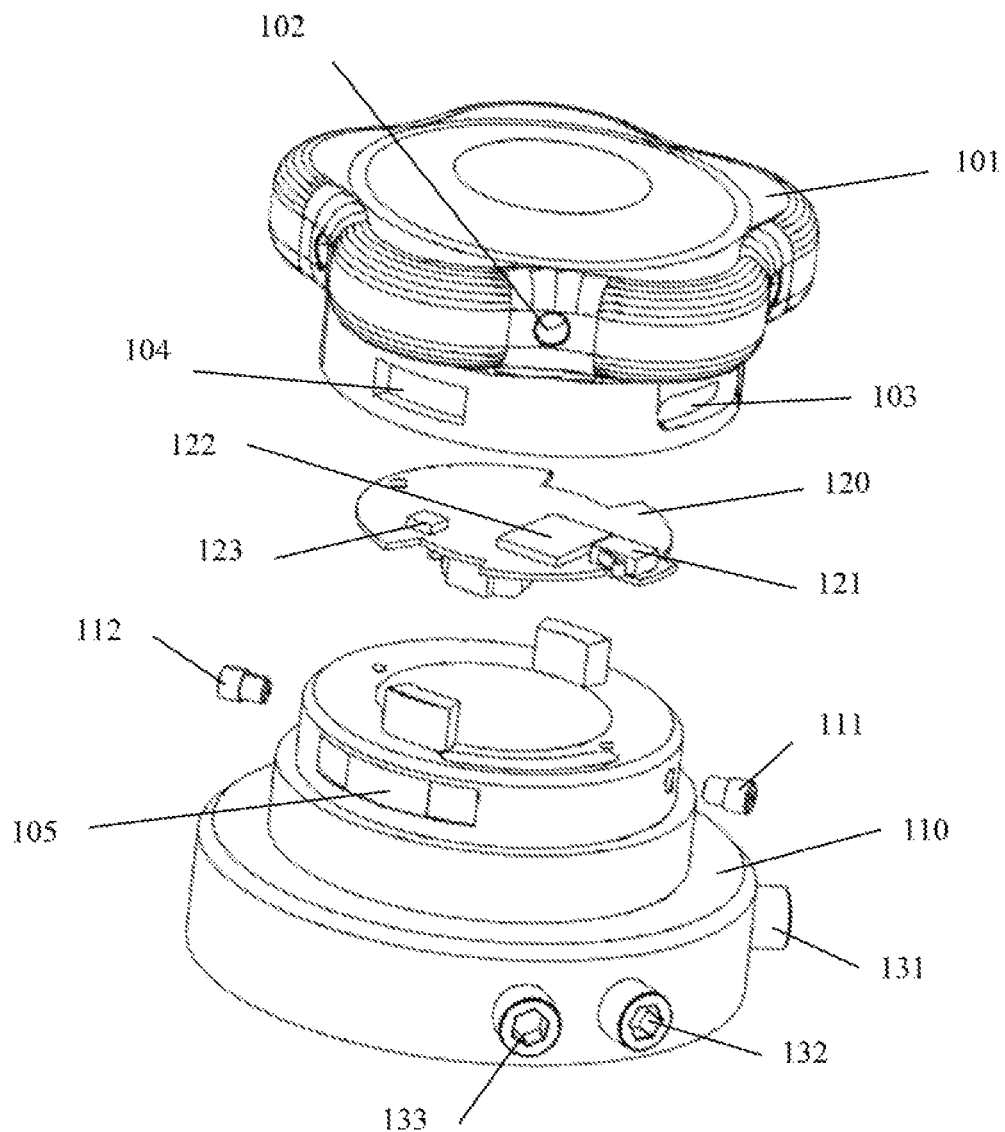
FIG. 2B is the bottom view of the smart cap shown in FIG. 2A. The center fixture can be directly engaged with the handwheel of the mechanical valve.
FIG. 2C is the bottom view of the smart cap shown in FIG. 2A. Instead of direct engagement to the mechanical valve handwheel, the shape specially designed is able to directly replace the handwheel, and to make the installation easily as a plug-and-play feature.
Figure 2B:
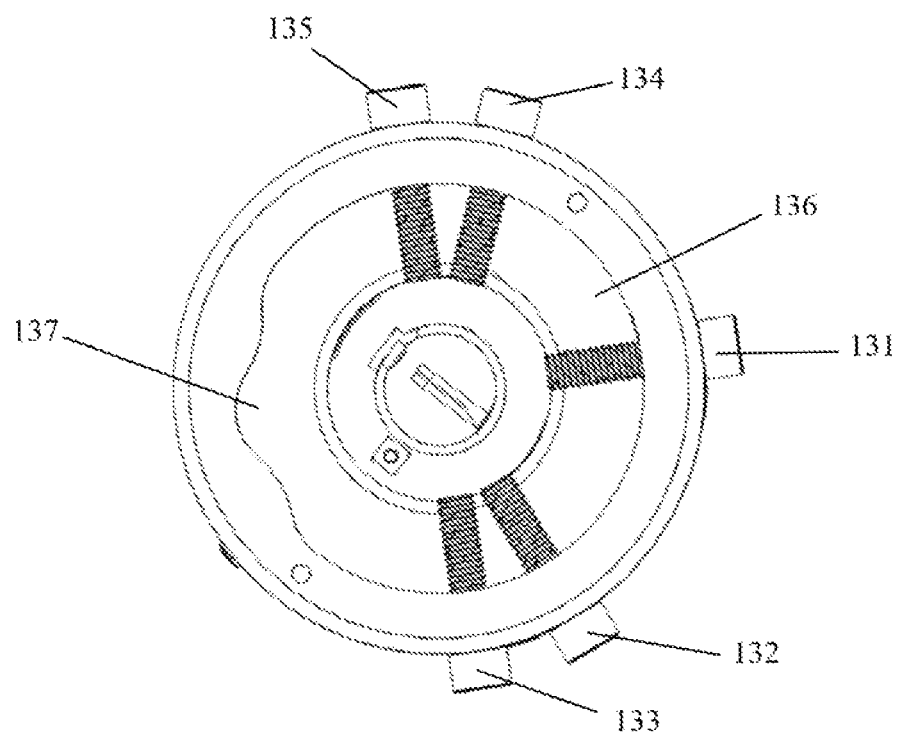

For the current art, the valve 010 on each gas cylinder is simply controlled via a hard plastic or metal handwheel (FIG. 1). The handwheel 010 is fixed to the valve via a cuboid stem 030 at the center of the handwheel. There is no indication of the valve status, and it could often confuse the users as for whether the valve is at open or close status with bare eyes even at the proximity. For the preferred embodiment, the present disclosure of a digital gas cylinder cap combined with a mass flow meter integrated with the digital data collector from an iBeacon module or a RFID reader, and remote data transmission capability for a single gas cylinder or a plural number of gas cylinders, which can effectively deliver the information to the user for the gas cylinder open/close status as well as the actual gas consumption in a specific gas cylinder. The information transmitted from the digital cylinder management system to the user and/or supplier can be via a variety of remote data options or the available Internet of Things (IoT) protocol. The explosive view of the said digital gas cylinder cap is shown in FIG. 2A, where each component of the said smart digital cap is disclosed. The handwheel or the handle 101 shall be made with metal or enhanced fiber or other hard plastic materials providing the necessary applicable force to the open/close of the valve in the relevant environments. 102 is an opening for the wireless data transmission in the iBeacon configuration to ensure no blockage of wireless signals, this is particularly necessary if the build material is metal. Such opening shall be plural in order to have effective signal transmission. In FIG. 2A, five openings are symmetrically placed around the smart cap topside. Apparently, other plural numbers of the openings are also opted depending on the shape of the design of the smart cap. 103 and 104 are two windows that shall display the color bar code (105). The preferred color bar code 105 shall be red and black standing for "open" and "close" of the gas cylinder valve where the said smart cap is installed. For the user's preference or other purpose of identification, other colors can also be used. The mechanical signs shall help the operator easily and efficiently identify the gas cylinder status at the proximity such that the mistakes to backfill empty gas cylinders due to accidental opening of a new gas cylinder before closing of all empty gas cylinders can be eliminated. 110 is the base of the said smart gas cylinder cap, which has the functionality to engage the existing handwheel of mechanical valve so that the gas cylinder company will not necessarily change the current design of the mechanical gas cylinder valve handwheel. The screws 111 and 112 are used to limit the movement range of the smart cap handwheel 101 and allow the windows 103 and 104 are traveling to the correct positions to indicate the red color bar code for valve open status and black bar code when 101 is reversed to cylinder valve close status. The 120 is the printed circuitry board that hosts the electronic data transmission of the said smart gas cylinder cap. The 121 is the micro-switch with a touch pin. When the said smart gas cylinder cap is installed onto a new gas cylinder, this micro-switch stays at the open state, and when the said smart gas cylinder cap is rotated to engage the mechanical valve, and then proceed further to the open status, the handwheel will trigger the micro-switch 121 into the close state and further initiates the iBeacon 122 that shall start to broadcast the data such as the serial number and position of the valve. The relevant valve information is pre-programmed via a microcontroller 123 and other associated electronics.

Figure 2C:
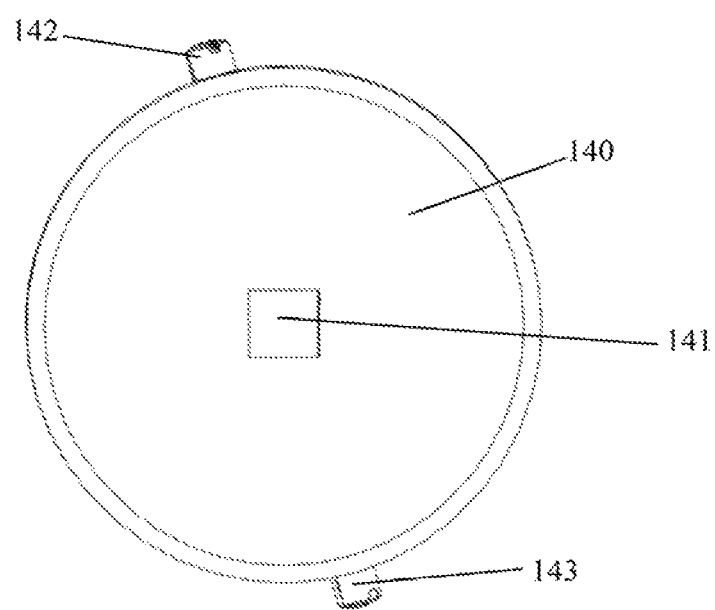

The 131, 132 and 133 are a plural number of screws that are used to fix the smart cap engaged to the existing mechanical valve handwheel that are further explained in FIG. 1B. The existing mechanical valve handwheels can have variety of shapes. In order to tightly grasp the mechanical handwheels via the designed smart valve base, the shape of the base bottom that is in direct engagement with the mechanical handwheel will have half rounded curvature 136 and half petal shape 137. With this structure, any shape of mechanical handwheel can be engaged with the petal while the plural number of the screws will enforce the engagement. For this purpose, additional screws 134 and 135 which are placed symmetrically to those of 132 and 133. In case that the gas cylinder is delivered without a mechanical handwheel or the mechanical handwheel can be easily removed, the engagement base unit of the said smart gas cylinder cap can be simplified as shown in FIG. 2C where only the bottom sketch of the base portion of smart gas cylinder cap is shown. The simplified smart cylinder cap base unit 140 with a cuboids stem 141 is made at the center of the base, and two screws 142 and 143 are used to fix the base directly onto the cuboids valve stem which is attached to the gas cylinder.

Figure 3A:
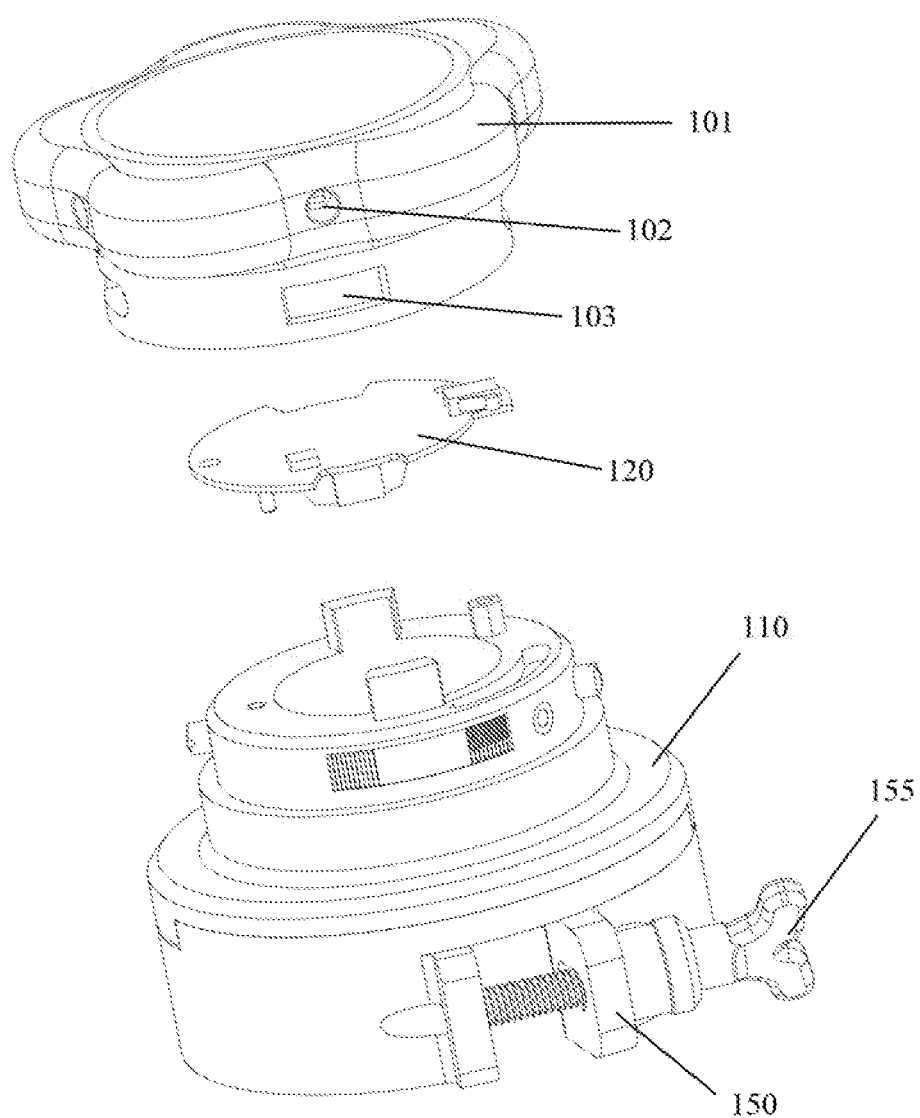
FIG. 3A is the explosive view of the alternative design of FIG. 2A, A single butterfly screw replaces the multiple screws.
Figure 3B:
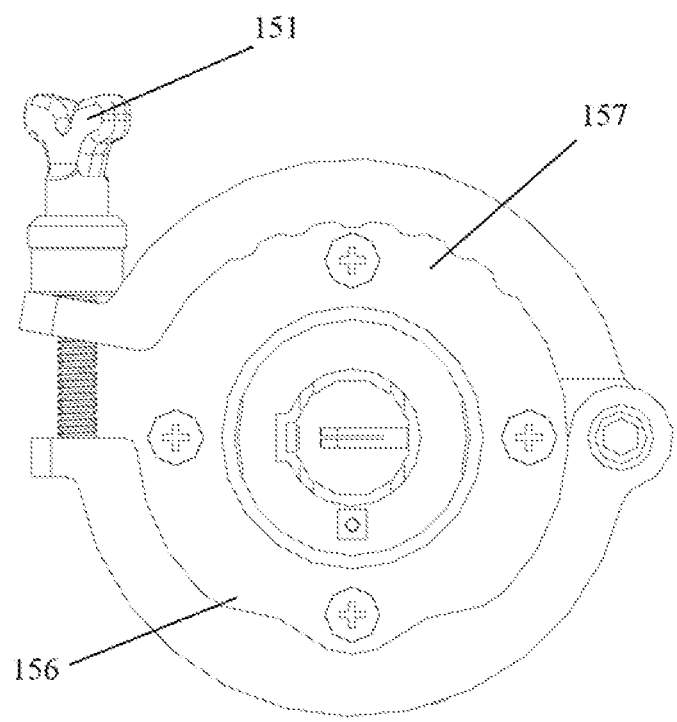
FIG. 3B is the bottom view of the smart cap shown in FIG. 3A.

For the preferred embodiments, the base of the said smart gas cylinder cap 110 is used to engage the mechanical valve handwheel. Using the screws to achieve the engagement is an option but in many actual cases, the gas cylinders could be placed isolated and access to the tooling would not be feasible. Therefore, it is desired to design an alternative approach for the engagement as shown in FIG. 2A where the engagement base portion is replaced with a metal spring configuration 150. The butterfly screw 155 is used to fasten the spring, instead of using the push-in screws with a screwdriver as shown in FIG. 1B. For the best performance, the base spring 150 is preferred to be made of hardened metals, such as steel, non-ferrous metals such as bronze or titanium or hard plastics for the cost-effective approaches. The shape for the engagement to the mechanical valve handwheel is preferably similar to those previously described as shown in FIG. 3B. Half of the shape shall be in the shape of a petal 156 which provides the flexibility to engage with different shapes of mechanical valve handwheel, while the another half of the shape is in the proximity of a round one 157 which provides the smooth holding while the spring is tightened with the butterfly screw handle.

Figure 4:
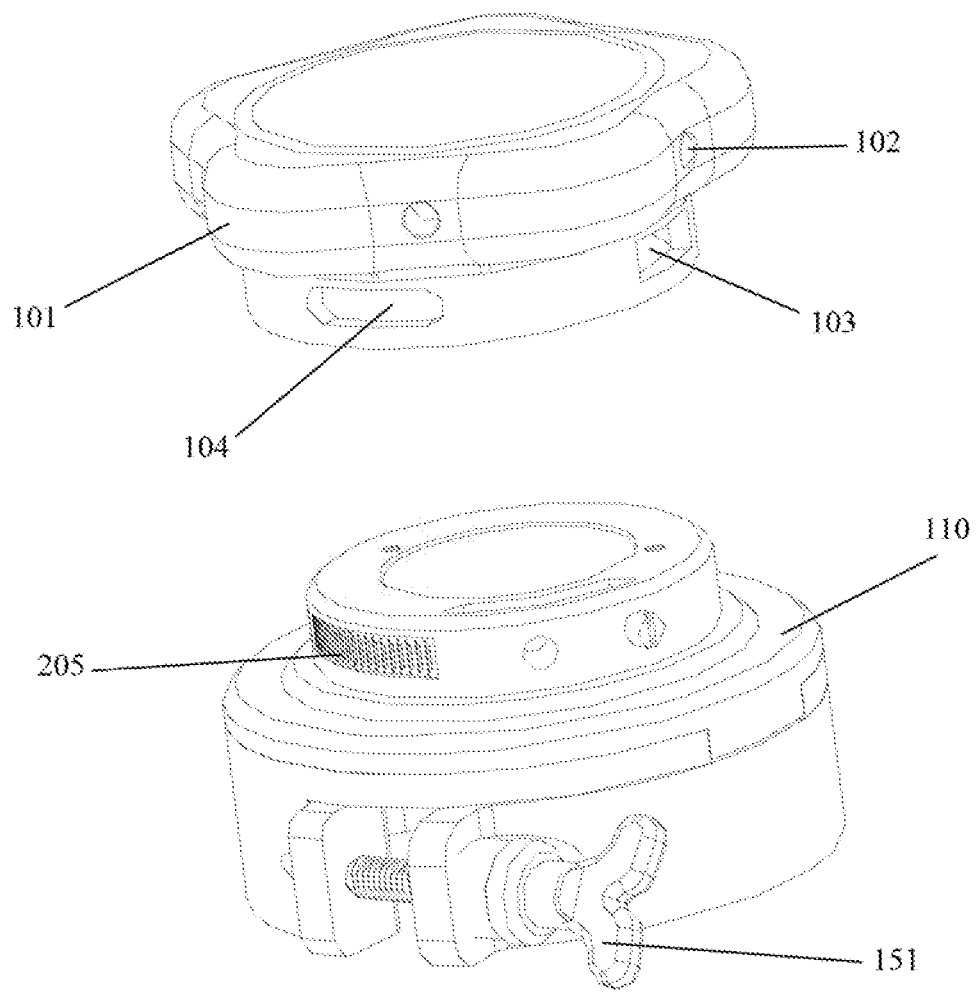
FIG. 4 is the explosive view of the smart cap with the RFID status indicator as well as the mechanical indicators for its status.

The smart gas cylinder cap with an iBeacon data broadcasting mode can effectively provide the gas cylinder status whether the gas cylinder is in use and possibly the pinpointed location of the gas cylinder if the installation of the said smart gas cylinder cap is registered and the iBeacon data is properly programmed. The iBeacon mode, however, has one disadvantage that it must have an external source or a battery for the operation. Therefore, in another preferred embodiment, a RFID is applied to replace the iBeacon option. In FIG. 4, a dual RFID 205 is placed at the same location where the color bar codes are placed (FIG. 2A). The dual RFID will be displayed when the handwheel of the said smart gas cylinder cap is turned either towards open or close direction of the valve via the windows 103 or 104, respectively. The dual RFID will carry the codes for open and close states as well as the valve serial number. When the valve is turned to open position, the "valve open" portion of the dual RFID will be displayed in the window. And the gas will be started to be delivered via the gas cylinder and the flow rate will be sensed by the MEMS smart mass flow meter in which an RFID reader is integrated. Once the flow rate is registered by the mass flow meter, the meter will trigger a wakeup call to the RFID reader which will scan the readable RFID and register the ID of the gas cylinder and its (open) status. Such information together with the current gas flow rate as well as the gas consumption data will then be transmitted via the concentrator or other wireless data relay approach to the designated data center. Once the RFID data are acquired, the RFID reader will turn into sleep mode to preserve the power, and for the same reason, once the data transmission is completed, the data concentrator or other wireless data transmission module inside the MEMS mass flow meter shall be turned into inactive mode. On the contrary, when the valve is turned into the close position, the "valve close" portion of the dual RFID will be displayed through the window while the "valve open" portion of the RFID will be hidden by the handwheel. Simultaneously, the MEMS mass flow meter shall register a zero flow rate, which will then subsequently wakeup the RFID reader and wireless data transmission module for acquiring the gas cylinder ID and status at the close status, and then transmit the gas cylinder information, the gas consumption and other relevant information such as date and time to the designated data (cloud) center for further data process. Apparently, the advantage of using an RFID to replace the microswitch plus iBeacon configuration is that the RFID will not require any external power and hence the said smart gas cylinder cap can be used as long as the normal wear of degradation is allowed.

Figure 5:
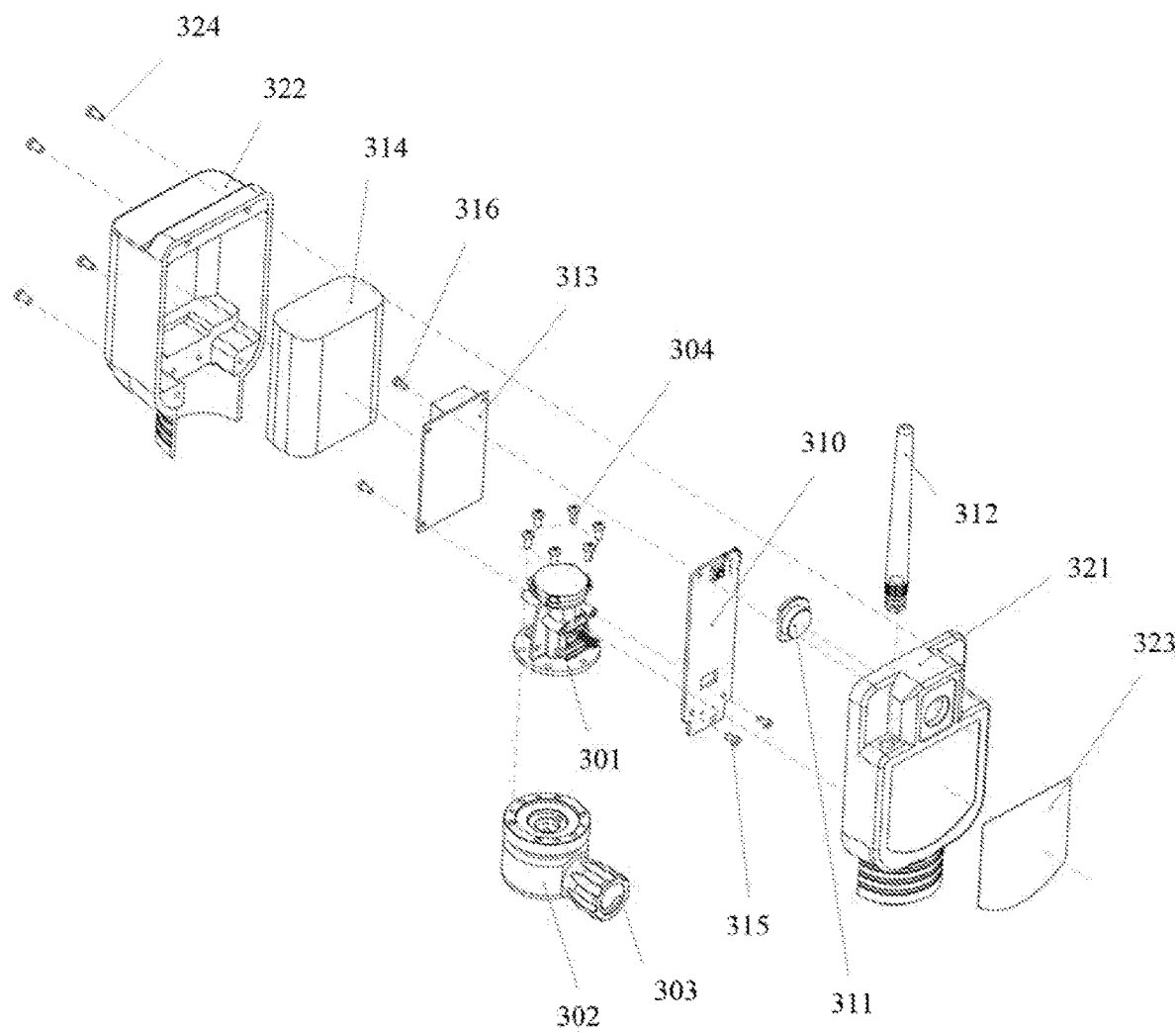
FIG. 5 is the explosive view of the smart MEMS mass flow meter that is integrated with a concentrator for various wireless data transmission. The concentrator relays the data further to the designated cloud, and alternatively a RFID reader is also integrated in case RFID smart valves are deployed in the system.

For the preferred embodiment, the MEMS mass flow meter shall be composed of several key components in FIG. 5 to accomplish the functionality as described above. 301 is the central metrology unit where the MEMS sensing chip is assembled to one of the flow channels and register the actual flow rate via the calibration of the final product. 302 is the mechanical interface to the flow channel connections and the associated mechanical flow rate adjustment valve 303 which can or cannot be a secondary regulator for the gas delivery. The flow rate metrology unit 301 is attached and fixed to the mechanical interface 302 via a plural number of screws 304. The electronics are integrated on the printed circuitry board, PCB 310 which include the signal conditioning circuitry and control electronics for the MEMS sensing element, a central process unit (CPU), the Bluetooth data acquisition module, or an RFID reader, and the wireless data relay module. The preferred wireless data relay module shall be compatible with the wireless communication standard of LoRa, NB-IoT, GSM, Sigfox, WIFI or other available data standard. The PCB shall also have a coin battery for timer or clock and data safety backup. The button 311 that is installed on the top of the PCB is served as a reset function of the MEMS mass flow meter, which can be enabled when there is a need for data reset or at the initial installation. 312 is the antenna for the wireless data relay, and 313 is another PCB that is used to provide the interface to the battery power pack 314. The battery pack is preferred to be lithium ion with a voltage of 3.6 Vdc and a high capacity of over 10 ampere hours. 315 and 316 are the other plural number of screws used to fix the PCBs to the meter central metrology unit which is assembled onto the mechanical interface. 321 and 322 are the front and back cover for the complete mass flow meter which are further installed on the mechanical flow channel interface and fixed with the plural number of screws 324. And finally, the meter tag 323 with specifications is attached to the front cover 321.

Figure 6:
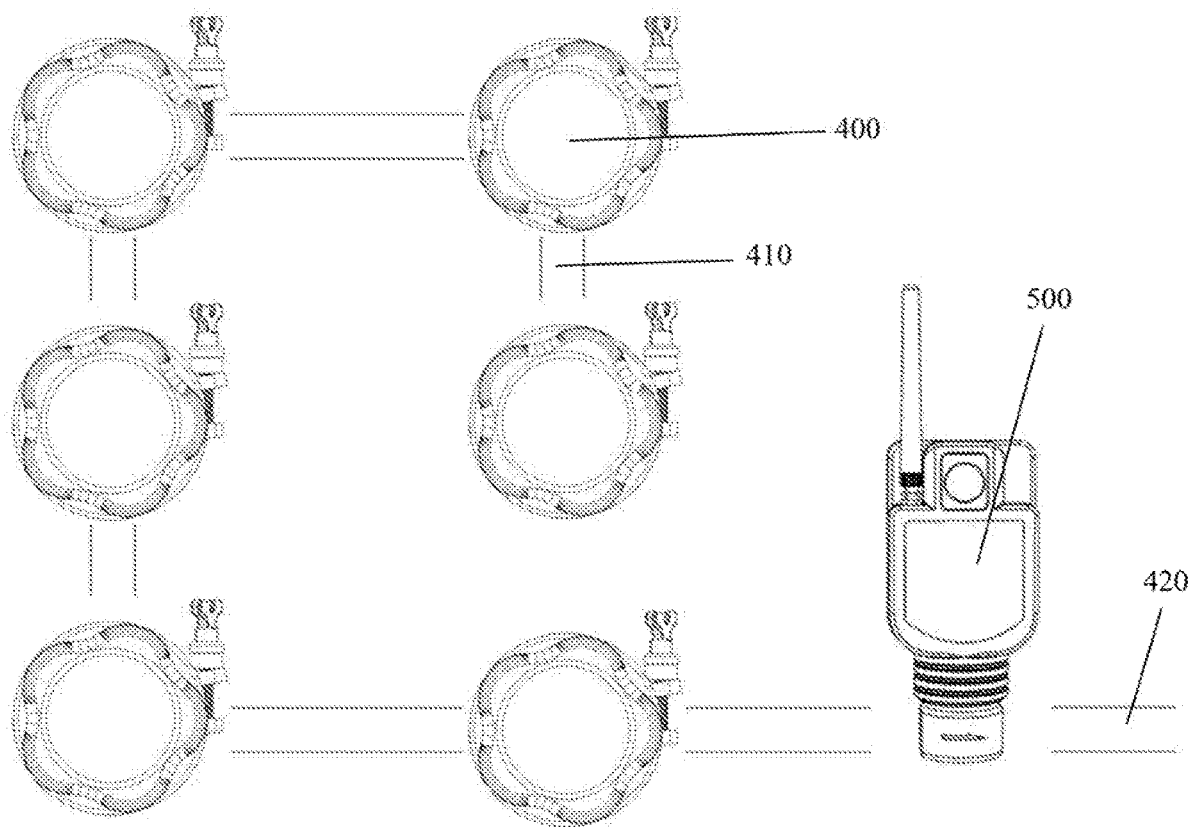
FIG. 6 is the schematic of the connected smart caps and the smart MMES flow meter system.

To further elaborate the system of the above preferred embodiments, FIG. 6 exhibits the configuration when the said smart gas cylinder cap(s) are connected in serial and with the smart MEMS gas flow meter integrated with the Bluetooth reader or RFID reader as well as a wireless data transmitter. In the preferred embodiment, the disclosed smart gas cylinder caps 400 are connected in serial with the gas pipe 410, and the inlet of the MEMS mass flow meter 500 is connected to the last gas cylinder in the serial. The gas cylinder can be a single one or in a plural number. The outlet of the MEMS mass flow meter is then connected to the delivery gas pipeline 420.

Figure 7:
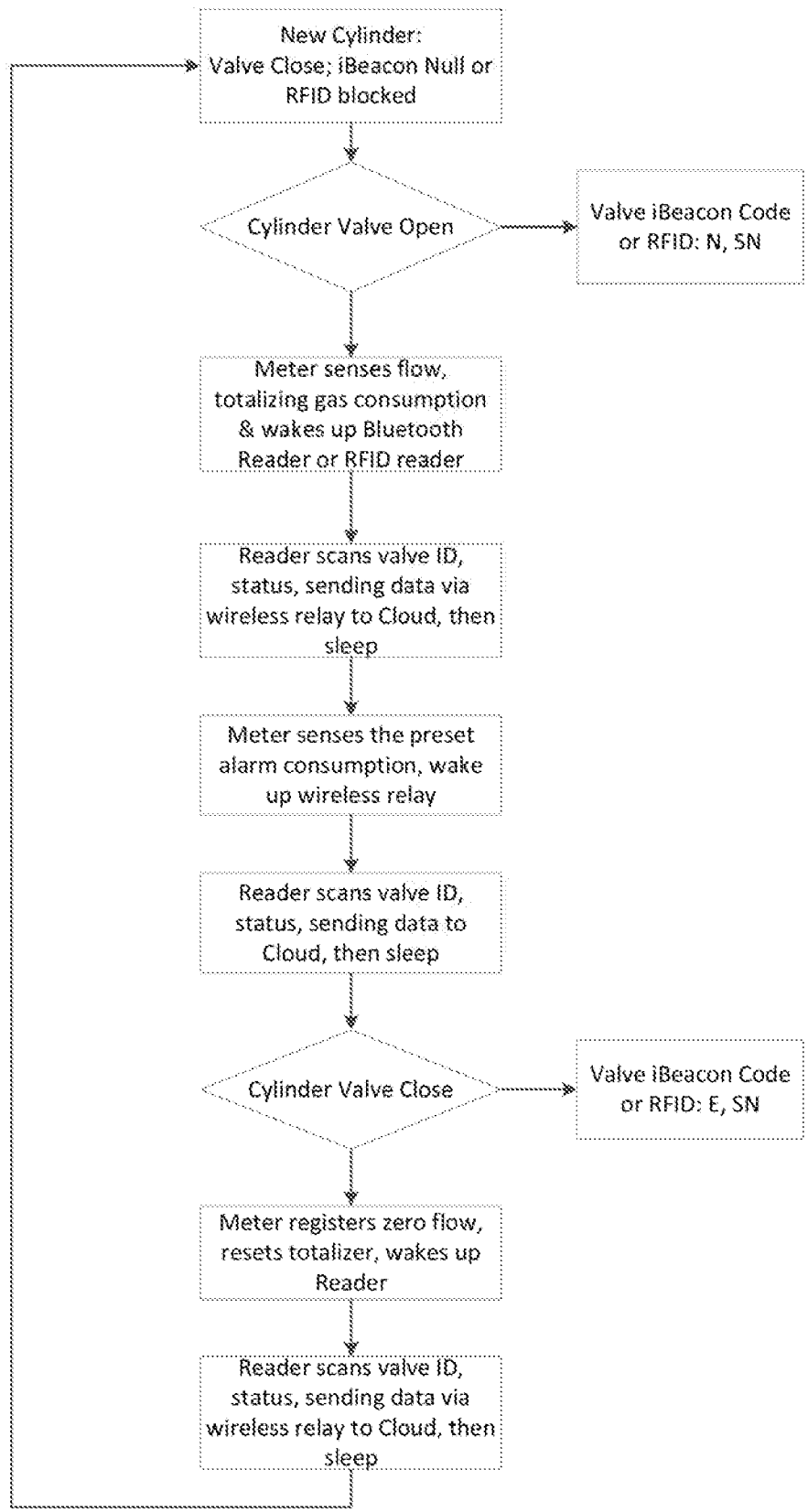
FIG. 7 is the operational logic flow chart for the smart cap using iBeacon or RFID for valve status data transmission which is coupled with a smart MEMS mass flow meter with an iBeacon reader or a RFID reader and data concentrator.

FIG. 7 is the flowchart that elaborates the details of the working procedure of the disclosed smart gas cylinder caps together with the MEMS mass flow meter integrated with a Bluetooth or RFID reader and a wireless data transmitter. For any gas cylinder installed with the said smart gas cylinder cap which is either engaged with the existing mechanical handwheel or directly installed onto the valve stem, the initial status of the gas cylinder before usage is defined by the said smart gas cylinder cap. In case an iBeacon mode is adapted, iBeacon will not work before the valve is opened. For the option with the RFID, the RFID code will be blocked by the cap and the color bar code window will not display any information. When the handwheel of the smart gas cylinder cap is turned into open position, for the iBeacon option, the micro-switch will be triggered, which will subsequently enable the iBeacon module to start transmitting the data of "N" (new) and the serial number or other pre-programmed related cylinder information such as gas type or gas composition. The color bar code will simultaneously display the red color bar code. As the gas will start to be delivered with an open valve, the MEMS mass flow meter will start to measure the gas flow rate and totalized gas consumption, which will subsequently wake up the Bluetooth iBeacon reader integrated inside the mass flow meter. The iBeacon reader will then acquire the data from the said smart valve cap. Once the data acquisition is complete, the microcontroller unit inside the mass flow meter will wake up the wireless data transmitter module such as LoRa, NB-IoT, GSM, Sigfox, WIFI or other desired and pre-embedded option that is also integrated inside the mass flow meter, and both the gas cylinder status, the gas flowrate and gas consumption data shall be sent to the designated data center or data cloud for further data process. The data can also be sent to the gas cylinder suppliers if desired and pre-programmed. After the completion of the data transfer, the microcontroller unit will disable the Bluetooth valve data acquisition and wireless transmission function and only allow the gas flow data acquisition to continue for the best power performance if the complete unit is powered by battery. For the said smart gas cylinder cap with an embedded RFID, when the handwheel of the smart gas cylinder cap is turned into open status, the RFID bar code encoded with the "N" (new) and the serial number and other related information such as gas type or composition of the gas cylinder will be displayed via the mechanical window. The opened valve will allow the gas to start delivery, and the MEMS mass flow meter will start to measure the gas flow rate and totalized gas consumption, which will subsequently wake up the RFID reader integrated inside the mass flow meter. The RFID reader will then acquire the data from the smart valve cap. Once the data acquisition is complete, the microcontroller unit inside the mass flow meter will wake up the wireless data transmitter module such as LoRa, NB-IoT, GSM, Sigfox, WIFI or other desired and pre-embedded option that is also integrated inside the mass flow meter, and the gas cylinder status, the gas flowrate and gas consumption data shall be sent to the designated data center or data cloud for further data process. The data can also be sent to the gas cylinder suppliers if desired and pre-programmed. Similarly, the RFID data acquisition and wireless data transmission will then be disabled. From time to time, the user may want to preset and gas consumption alarm or gas empty alarm that can be pre-programmed or registered in the MEMS mass flow meter. When the gas consumption measured by the mass flow meter for a specific or a plural numbers of gas cylinders matches to the preset alarm value, the microcontroller unit inside the mass flow meter will wake up the wireless data transmitter and relay the data to the designated data center or data cloud for further data process. After this task is complete, the microcontroller unit inside the mass flow meter will allow the wireless data transmitter back to the sleep mode for better power conservation. When the user received the alarm, an operator shall be sent to the site to close the empty gas cylinder(s) before starting to open the valve(s) of the new gas cylinder(s). Once the mass flow meter registers a zero flow from the normal flow rate metering, the microcontroller unit inside the mass flow meter shall wake up the iBeacon reader or RFID reader to capture the information of the gas cylinder(s) that is turned from open to close status. For the option with the iBeacon module, the micro-switch will again trigger the iBeacon module to start the transmission of the new code which is indicating an empty or used gas cylinder together with its serial number and other related information while the mechanical display window will then display a color bar code of "Black" for a closed valve or used gas cylinder. And for the RFID option, the same mechanical window will change to the "close" RFID bar code for the RFID reader to acquire. When the acquired smart gas cylinder valve via the cap information is received by the mass flow meter, the microcontroller shall wakeup the wireless data transmission module and relay the data to the designated data center or data cloud for further data process. After the completion of the procedure, the system shall return to its original status for a new operation. For the M EMS mass flow meter integrated also with a gas composition sensor, the gas type detection shall be active when the flow rate starts to be registered. This information can also be sent to the user once programmed.

For the additional preferred embodiment, the said smart gas cylinder cap and the MEMS mass flow meter system for those in the art shall become readily and apparently, and could be further incorporated with additional features such as an electrical driving valve for remote operation. It shall also be readily and apparently that the said smart gas cylinder cap and the MEMS mass flow meter system shall also be equipped with other available communication tools such as a wired connection option to interact with a local router or station for a large scale of clusters of the gas cylinder management with the disclosed smart gas cylinder cap and mass flow meter apparatus.

The invention claimed is:

1. A smart gas cylinder cap system including a smart gas cylinder cap and a MEMS mass flow meter for providing an existing gas cylinder with a handwheel an open/close status and gas consumption data to a user or a cloud data center comprising: the smart gas cylinder cap comprising:
    a gas cylinder valve handwheel engagement holder positioned over the existing handwheel of the gas cylinder,
    an electronic circuitry (120) with a mechanical micro-switch (121) positioned on the handwheel engagement holder,
    a Bluetooth iBeacon data broadcasting module provided on the electronic circuitry of the handheld engagement holder,
    a lithium ion coin battery mounted on the electronic circuitry;
    a replacement handwheel (101) provided on top of the handwheel engagement holder with two mechanical display windows (103);
        wherein, the electronic circuitry is enclosed between the replacement handwheel and the handwheel engagement holder,
    the MEMS mass flowmeter (500) comprising:
        a central metrology (301) unit; wherein the central metrology unit comprising:
        a MEMS sensing chip which is assembled to a flow channel; and
        a printed circuit board (PCB) circuitry (310) comprising:
        a central process unit (CPU),
        a Bluetooth data acquisition module enabled or disabled by the central process unit (CPU) in the PCB circuitry (310); and
        a wireless data acquisition module enabled or disabled by the central process unit (CPU) in the PCB circuitry (310).

2. The smart gas cylinder cap system of claim 1, wherein the gas cylinder valve handwheel engagement holder is made of hard metal with spring properties selected from options of hard stainless steel, aluminum alloy, or hard plastics; in order to assure applicable engagement for most existing mechanical handwheels on gas cylinders, shape of the gas cylinder valve handwheel engagement holder that is in direct contact with existing mechanical handwheel is having its one half with a petal shape and another half with a rounded shape; the petal shape is to match or grasp any handwheel shape while the rounded shape is to press tightly against the mechanical handwheels of gas cylinders; a plural number of set screws are symmetrically distributed at the half of rounded shape of the engagement holder to engage on the original mechanical handwheel of gas cylinder.

3. The smart gas cylinder cap system of claim 1, wherein the Bluetooth iBeacon data broadcasting module of the smart gas cylinder cap is triggered by the mechanical micro-switch which is benefited by no need of additional power consumption; the Bluetooth iBeacon data broadcasting module is wirelessly connected to the central process unit (CPU) of the MEMS flow meter that can be used to program desired information of each gas cylinder including one of a serial number, a valve position and applicable gases; the Bluetooth iBeacon data broadcasting module is powered by the lithium ion battery to provide power for a period of time.

4. The smart gas cylinder cap system of claim 1, wherein the replacement handwheel includes a color barcode of two colors that are used to represent status of the gas cylinder for an onsite operator.

5. The smart gas cylinder cap system of claim 1, wherein the replacement handwheel includes a plural number of openings close to the Bluetooth data acquisition module such that iBeacon Bluetooth data transmission will not be blocked; the openings are distributed symmetrically; the handwheel is made of one of a hard plastic materials or light metal.

6. The smart gas cylinder cap system of claim 1, wherein the cylinder valve handwheel engagement holder made as a base unit can be directly placed on the existing handwheel of the gas cylinder; the base unit can be made with a mechanical cuboids that can directly engage with a stem of the gas cylinder handwheel to reduce weight and height of the smart gas cylinder cap.

7. The smart gas cylinder cap system of claim 1, wherein the Bluetooth iBeacon data broadcasting module can be replaced with an RFID alternative approach; the RFID is in dual code mode or with two RFIDs; one has a code to represent for open status of the gas cylinder and another code to represent for empty status of the gas cylinder.

8. The smart gas cylinder cap system of claim 7, wherein the RFID of the smart gas cylinder cap can go into sleep mode in order to keep lower power consumption.

9. The smart gas cylinder cap system of claim 1, wherein the MEMS mass flow meter is operated by one of a calorimetric measurement principle or by other measurement principles including one of time-of-flight or thermal anemometry.

10. The smart gas cylinder cap system of claim 1, wherein the MEMS sensing chip is placed and assembled in a bypass gas channel inside the metrology unit, which can make the MEMS mass flow meter compact and beneficial for higher flow measurement.

11. The smart gas cylinder cap system of claim 1, wherein the Bluetooth data acquisition module has low power consumption characteristics; the central process unit (CPU) that acquires metrology data from the MEMS sensing chip is also used to enable or disable the Bluetooth data acquisition module to acquire the data from the Bluetooth iBeacon data broadcasting module of the smart gas cylinder cap, and it can also go into sleep mode in order to keep lower power consumption.

12. The smart gas cylinder cap system of claim 1, wherein the wireless data transmission module can go into sleep mode in order to keep lower power consumption.

13. The smart gas cylinder cap system of claim 1, wherein protocols for the wireless data transmission module can be selected from one of LoRa, NB-IoT, GSM, Sigfox or WIFI.

14. The smart gas cylinder cap system of claim 1, wherein the smart gas cylinder cap can be a single or a plural number; the smart gas cylinder cap system only requires one MEMS mass flow meter to work functionally.

* * * * *